United States Patent [19]
Shinomura et al.

[11] Patent Number: 5,295,485
[45] Date of Patent: Mar. 22, 1994

[54] ULTRASONIC DIAGNOSTIC SYSTEM

[75] Inventors: Ryuuichi Shinomura, Higashimatsuyama; Wasao Takasugi, Higashiyamato; Yoshikuni Matsunaga, Hachioji; Kageyoshi Katakura, Tokyo, all of Japan

[73] Assignee: Hitachi, Ltd., Tokyo, Japan

[21] Appl. No.: 986,905

[22] Filed: Dec. 8, 1992

[30] Foreign Application Priority Data

Dec. 13, 1991 [JP] Japan ............................... 3-330265

[51] Int. Cl.⁵ .............................................. A61B 8/00
[52] U.S. Cl. ............................................... 128/660.07
[58] Field of Search ............... 128/660.07, 660.08, 128/660.01, 661.01, 662.03, 660.09, 710; 73/620, 625, 626

[56]  References Cited
U.S. PATENT DOCUMENTS

| | | | |
|---|---|---|---|
| 3,964,296 | 6/1976 | Matzuk | 73/625 |
| 4,246,792 | 1/1981 | Matzuk | 73/620 |
| 4,542,653 | 9/1985 | Liu | 73/626 |
| 4,715,385 | 12/1987 | Cudahy et al. | 128/710 |
| 4,722,345 | 2/1988 | Ueno et al. | 128/660.09 |
| 5,125,409 | 6/1992 | Kajino et al. | 128/660.07 |
| 5,152,290 | 10/1992 | Freeland | 128/660.07 |

FOREIGN PATENT DOCUMENTS

| | | | |
|---|---|---|---|
| 55-151952 | 11/1980 | Japan | A61B 10/00 |
| 57-170230 | 10/1982 | Japan | A61B 10/00 |
| 62-227326 | 10/1987 | Japan | A61B 8/00 |
| 3-23853 | 1/1991 | Japan | A61B 8/14 |

*Primary Examiner*—William E. Kamm
*Assistant Examiner*—George Manuel
*Attorney, Agent, or Firm*—Antonelli, Terry, Stout & Kraus

[57] ABSTRACT

An ultrasonic diagnostic system includes a probe composed of a group of transducers for transmitting and receiving an ultrasonic wave, a main system connected with the probe by a cable, a memory card, and a battery pack for supplying power. The ultrasonic diagnostic system further includes a data processing unit and a monitor which are provided separately from the above components. The probe and main system are prepared for each ultrasonic scanning mode. The data processing unit subjects the received signal data recorded in the memory card to sophisticated data processing which cannot be carried out by the main system thereby to display the processing result. An examiner can carry the probe, main system, memory card and the battery pack for supplying power instead of a stethoscope to acquires diagnosis data and can process a suspicious image in diagnosis at bedside or house call using the data processing unit thereby to implement precise diagnosis.

20 Claims, 9 Drawing Sheets

ULTRASONIC DIAGNOSTIC SYSTEM

BACKGROUND OF THE INVENTION

The present invention relates to a medical ultrasonic diagnostic system, and more particularly to a handy ultrasonic diagnostic system which a doctor can carry in place of a stethoscope.

Previously known ultrasonic diagnostic systems are generally large-sized, and compact systems can be barely carried to bedside. These systems can be connected with plural kinds of probes such as a linear electronic scanning probe, a convex electronic scanning probe, a sector electronic scanning probe and a mechanical sector scanning probe. These systems were so structured that the above connectable several kinds of probes can provide the best image.

Several prior arts will be described briefly.

JP-A-55-151952 discloses a portable compact-size ultrasonic diagnostic system including integrated components, i.e., an electronic scanning probe having plural aligned piezo-electric materials, an electronic control unit for controlling the action of the probe, a display which is a CRT (cathode ray tube) and a power source for supplying an operational voltage to each part of this system. This reference also discloses an ultrasonic diagnostic system having a probe unit incorporating a probe, an electronic circuit for controlling it, a transmission section for transmitting an image signal by radio, a transmission antenna and a power source, and a display which is provided at a different member from the probe unit and receives the signal transmitted from the probe unit to display an image.

JP-A-57-170230 discloses an ultrasonic diagnostic system including a probe and a memory unit for temporarily storing an echo signal reflected from the probe to display its image by a television set, in which an examiner can select an ultrasonic moving image or a frozen image at the probe and which does not require any particular transmitted path for selecting the frozen image.

JP-A-62-227326 discloses an ultrasonic diagnostic system small-sized enough to carry in a pocket. This reference intends to provide a system which permits diagnosis information to be easily seen on a relatively wide display screen and is small-sized and light-weighted for easy carrying. To this end, the system is provided with a flat display for displaying the diagnosis information and a mechanism for housing it which serves to house it within the system body when the system is carried and extract it from the body when the system is used. The reference also discloses an ultrasonic diagnostic system provided with a probe attachment mechanism for attaching a probe to the system body so that an acoustic lens is inside when the system is carried.

Figure 9:
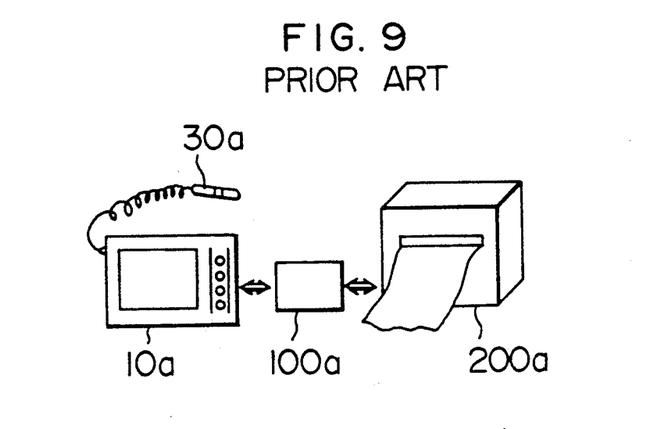
FIG. 9 is a pictorial view showing the arrangement of the conventional ultrasonic diagnostic system.
Figure 10:
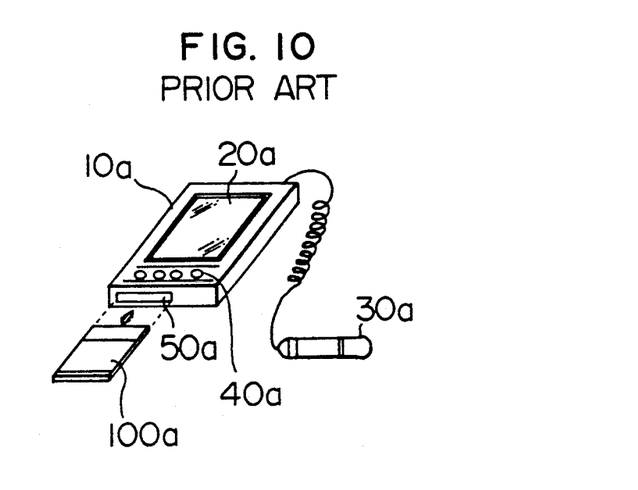
FIG. 10 is a perspective view showing the arrangement of the main system in the conventional ultrasonic diagnostic system.
Figure 11:
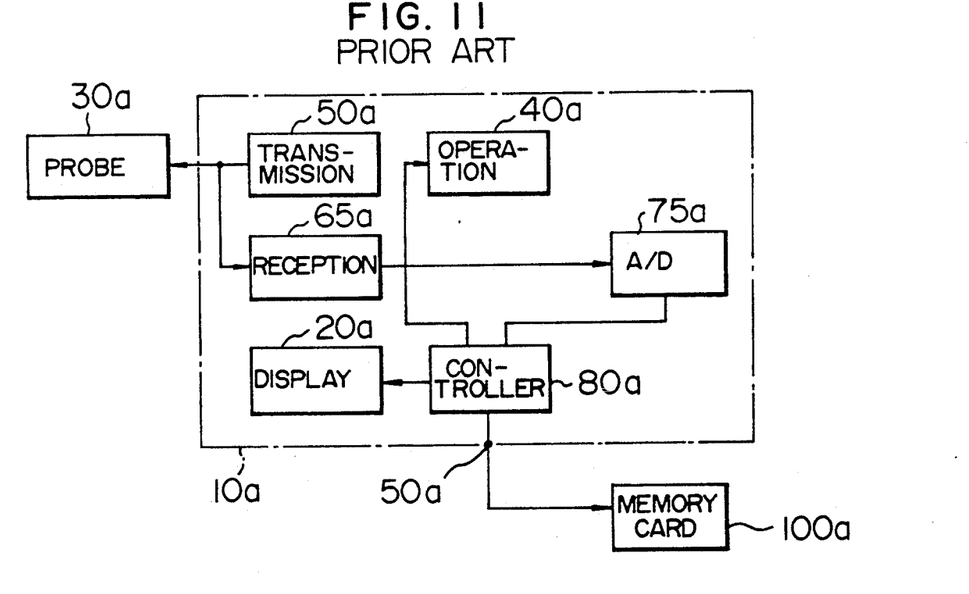
FIG. 11 is a block diagram showing the circuit configuration of the conventional ultrasonic diagnostic system.

JP-A-3-23853, as shown in FIGS. 9, 10 and 11, discloses an ultrasonic diagnostic system including an A/D converter 75a for converting an ultrasonic image signal inputted from a probe 30a into a digital signal, and a removable external memory device 100a. As clearly seen from FIG. 11, the system further includes a control unit 80a for reading the digital signal from the A/D converter 75a to be stored in the external storage medium 100a or controlling read of the stored data from the storage medium 100a, and a display 20a for displaying the digital signal from the control unit 80a. The reference also discloses an ultrasonic diagnostic system further comprising a recording equipment 200a for reading the data stored on the removable external memory device 100a to display them, or outputting them. This system image-processes a received echo signal to display the image of an examined part; stores, in the external memory device from removable from a system body 10a, the image data when a clear image has been obtained, directly or after they are stored in buffer memory; and as necessity requires, displays the image data or prints out the image data by setting the external memory device 100a in the recording equipment 200a. Thus, the system can be made compact and can hold the examination result without simultaneously carrying the recording equipment 200a and the system body 10a.

SUMMARY OF THE INVENTION

The systems according to the above prior arts leads to its large scale if high image quality is pursued in order to improve its diagnostic ability, and provides poor image quality if the circuit scale is restricted to reduce the system size.

JP-A-55-151952 that the image signal is transmitted from the probe by radio and received by the display section provided on a separate member to display the image, but does not refer to that the received signal data are stored and held on the external memory device and high image quality is acquired by a data processing unit which is provided separately from an ultrasonic image sensor means.

JP-A-57-170230 describes that the frozen image can be selectively changed at a desired time on the side of the probe, but does not refer to that the received signal data are stored and held on the external memory device and high image quality is acquired by a data processing unit which is provided separately from an ultrasonic image sensor means.

JP-A-62-227326 has a description relative to the flat display and housing of the probe within the system body, but does not refer to how the image data and the received signal data should be dealt with.

JP-A-3-238853 described that the probe is desired to be e.g. a mechanical sector type and one recording device can keep up with plural diagnostic devices. But this reference does not refer to that the main system conforms to plural kinds of ultrasonic scanning modes, and does not also refer to how the ultrasonic scanning modes are discriminated and the image data stored in the external memory device are discriminated for each person to be examined. Further, the reference describes that the recording device reads the image data stored on the external memory device to be outputted as an image, but does not refer to that the data stored on the external memory device are subjected to several kinds of image processing to improve image quality. Furthermore, the image data when a clear image is acquired by the main system are stored on the external memory device, and are outputted by the recording device. Since the main system and the recording equipment output the same image, if high image quality is pursued, the main system becomes large-scaled. In contrast, if the size of the main system is restricted, the image quality becomes poor.

The first object of the present invention is to provide an ultrasonic diagnostic system including a handy main system whose circuit arrangement is made small-sized, thus permitting an examiner to carry it in place of a stethoscope.

The second object of the present invention is to provide an ultrasonic diagnostic system in which a data processor provided separately from a main system processes the received signal data which are acquired by the main system and previously stored on an external memory device thereby to provide a higher quality image and thus several kinds of items such as a length, volume, area, attenuation, sound velocity and blood velocity can be measured.

The third object of the present invention is to provide a portable main system which permits an examiner to perform any operation such as outputting, inputting and erasing for the data stored in a desired segment of an external memory device, and provide the external memory device for transferring the data from or to a data processor which is provided separately from the main system.

In order to attain the above objects, the ultrasonic diagnostic system according to the present invention is structured as follows. The ultrasonic diagnostic system includes a main system composed of a signal processing part for processing the signal data received at a probe to provide an image, a display for displaying the image acquired, a data I/O port for sending the received signal data to an external memory device for storing them, a DC/AC converter for power supplied from a battery package into a necessary potential and a control part for each part of the main system; a probe for transmitting-/receiving an ultrasonic wave; the battery package for supplying power to the main system; an external memory device such as a memory card for recording or storing the received signal data from the main system; at least one data processing unit for reading the data from the external memory device and subjecting the read data to sophisticated data processing; and a monitor for displaying the data processing result. The data processing unit and monitor can process the received signal data at the probe in several kinds of ultrasonic scanning modes.

The main system which is applied to the signal from the probe in several kinds of ultrasonic scanning modes and can realize image display and signal processing is prepared individually for each scanning mode. The image display and signal processing in the main system are carried out for only the probe in a specific ultrasonic scanning mode.

The units such as the monitor, DC/AC converter and data I/O unit which can be commonly used irrespectively of the scanning mode are attached to a common body. A main system cartridge which is separate from the common body and composed of units such as the connection part of the probe and the signal processing unit which are different with the scanning modes is inserted into the common body so that it can be connected with each unit attached to the common body. Thus, the main system according to the scanning system can be prepared.

The external memory device includes a data record part where at least one of one image data, and an RF signal data or detected signal data necessary to create one image is recorded, and an information record part where an identification code (e.g. linear electronic scanning probe) for the main system, patient information data (e.g. ID's corresponding to a diagnosis date, examiner's name and patient's name, chart number, and disease history). The external memory device comprises plural segments each having a prescribed memory size composed of the data record part, the information record part and a flag record part for recording the presence or absence of data storage. The external memory device also includes a display for displaying whether or not the data have been stored in each segment. The display is so adapted that it can designate the segment which data should be stored in or erased from.

If the ultrasonic diagnostic system is structured as described above, it is possible to realize an ultrasonic diagnostic system which has a small circuit scale and is handy. Specifically, not only array transducers but also electronic circuits such as a transmitted-and-received circuit, a received amplifier, a receiving beam former and a control circuit are integrated within the probe, and a main system is dedicated to the ultrasonic scanning mode for the probe corresponding to each diagnosis object. For this reason, the circuit scale of the probe and the corresponding dedicated main system become small so that a handy ultrasonic diagnostic system can be realized.

Image data, or RF signal data or detected signal data necessary to create images are stored in the external memoriozed medium for the main system corresponding to several kinds of ultrasonic scanning modes. Since the data processing unit for reading the data stored on the external memory device and subjecting the read data to several kinds of sophisticated processing and a monitor are provided separately from the main system, high quality images can be realized. Thus, several kinds of items such as a length, volume, area, attenuation, sound velocity and blood velocity can be measured.

Further, the external memory device, e.g., the memory of a memory card is divided into plural segments, and the storage state in each segment is displayed. An examiner, therefore, can access desired data, regulate the data in the memory card and input data by erasing the designated image or using a new memory card when diagnosis is performed using the memory card short of storage capacity. Thus, the examiner can flexibly manage the external memory device.

DESCRIPTION OF THE PREFERRED EMBODIMENTS

Figure 1:
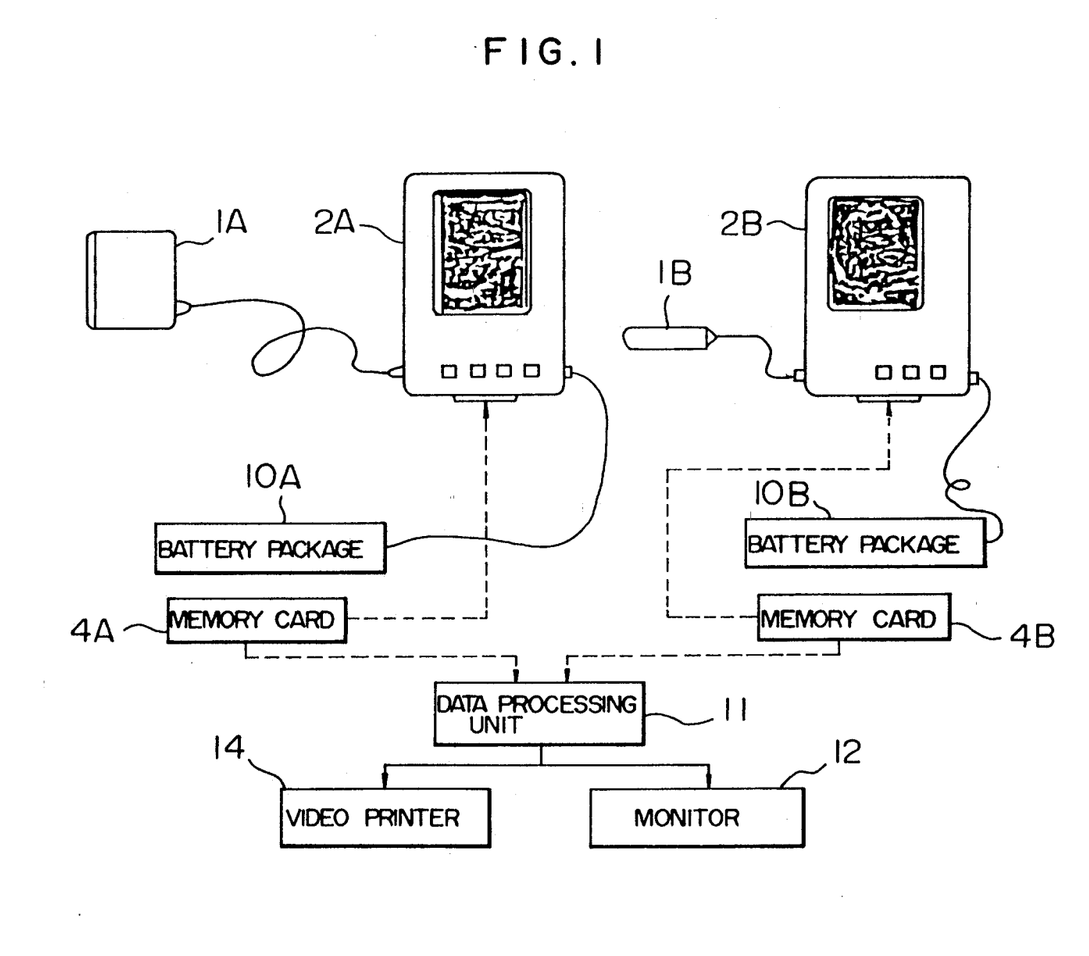
FIG. 1 is a pictorial and block diagram showing an arrangement of the ultrasonic diagnostic system according to the present invention.

Referring to FIG. 1, an explanation will be given of the entire concept of the ultrasonic diagnostic system according to the present invention.

The ultrasonic diagnostic system according to the present invention includes one or one group of probes 1A, 1B . . . , main systems 2A, 2B . . . each connected with the corresponding probe through a cable, memory cards 4A, 4B . . . , battery packages 10A, 10B, . . . , a data processing unit 11 and a monitor 12. The diagnostic system may further include a video printer 14 as necessity requires. The probes 1A, 1B . . . serve to transmit or receive an ultrasonic wave. The main systems 2A, 2B . . . serve to take in received signal data from the probes, process the data to display an image and send the image data o received signal data (RF signal data or detected signal data) to external memory devices 4A, 4B, . . . which are memory cards. The memory cards 4A, 4B, . . . serve to store the image data or received signal data, an identification code (e.g. linear electronic scanning probe) for the main system, patient information data (e.g. ID's corresponding to a diagnosis date, examiner's name and patient's name, chart number, and disease history). The battery packages 10A, 10B, . . . serve to supply power to the main systems 2A, 2B, . . . . The data processing unit 11 serves to read, from the memory cards 4A, 4B, . . . , the received signal data, the identification code for the main system and the patient information data and decide the ultrasonic scanning mode on the basis of the identification code for the main system to subject the read data to sophisticated data processing which cannot be carried out by the main systems. The monitor 12 serves to display the result of the data processing. The video printer 14 serves to output the result of the data processing. The main systems are prepared individually for respective ultrasonic scanning modes, and are used as pairs with the probes. For example, a probe and a main system are prepared for each of linear electronic scanning, convex electronic scanning, sector electronic scanning, mechanical sector scanning, etc. In diagnosis, the probe and the main system are used as a pair. The probe and main system may be fabricated as individual members and may be connected by a cable or connector. Otherwise, they may be formed integrally so as to be connected with each other by a cable, or they may be formed within the same case without using a cable.

FIG. 1 shows the case where two probes and two main systems are prepared for the linear electronic scanning and the mechanical sector scanning. The main system 2A is dedicated to the linear electronic scanning whereas the main system 2B is dedicated to the mechanical sector scanning. The memory cards 4A and 4B and the battery packages 10A and 10B may be used individually or commonly for the main systems 2A and 2B.

The data processing unit 11, monitor 12 and video printer 14 can used commonly for the memory cards 4A and 4B.

When a certain examiner makes diagnosis using the probe 1A and main system 2A dedicated to the linear electronic scanning, the image data or received signal can be stored on the memory card 4A. When another examiner makes diagnosis at another place using the probe 1B and main system 2B dedicated to the mechanical sector scanning, the image data or received signal can be stored on the memory card 4B having the same format as that of the memory card 4A. When the examiner sets the memory card 4A in the data processing unit 11 which are provided separately from the main systems 2A and 2B and designates a segment or area of the memory card 4A with the data stored by means of the main system 2A, the data processing unit 11 automatically identifies the ultrasonic scanning mode as the linear electronic scanning mode on the basis of the identification code for the main system 2A stored in the designated area, and performs the data processing for linear electronic scanning automatically or under the condition set by the examiner. Likewise, when another examiner sets the memory card 4B in the data processing unit 11 and designates a segment of the memory card 4B with the data stored by means of the main system 2B, the data processing unit 11 automatically identifies the ultrasonic scanning mode as the mechanical sector scanning mode on the basis of the identification code for the main system 2B stored in the designated area, and performs the corresponding data processing automatically or under the condition set by the examiner.

In the ultrasonic diagnostic system having the arrangement as shown in FIG. 1, the number of the main systems ia larger than that of the data processing unit 11. As necessity requires, the examiner selects a probe and a main system which signal-processes only the received signal data in accordance with the scanning mode for this probe, and makes diagnosis. When the examiner intends to make diagnosis using plural probes according to different scanning modes, he should prepare one battery package and main systems corresponding to the different scanning modes.

The data processing unit 11 provided separately from the main system 2A reads the data stored in the memory card 4A to subject the read data to more sophisticated data processing other than the signal processing performed in the main system 2A, and displays the image based on the data processing result on the monitor 12. As necessity requires, the data processing result may be outputted to the video printer 14 or several storage devices. Thus, by means of the data processing unit 11, the examiner can fulfill the processing (e.g. advanced interpolation processing, echo enhancement, $\gamma$-correction, optimization of a gain curve, correlation process, etc.) equivalent to a high performance ultrasonic diagnostic system thereby to obtain the high resolution image relative to a person to be examined, including advanced diagnosis information. Thus, by means of the data processing unit 11 in this embodiment, the examiner can convert the image noticed at bedside or in diagnosis such as house call into a more accurate diagnosis image. Incidentally, a DC power supply provided separately may be used instead of the battery package.

Figure 2:
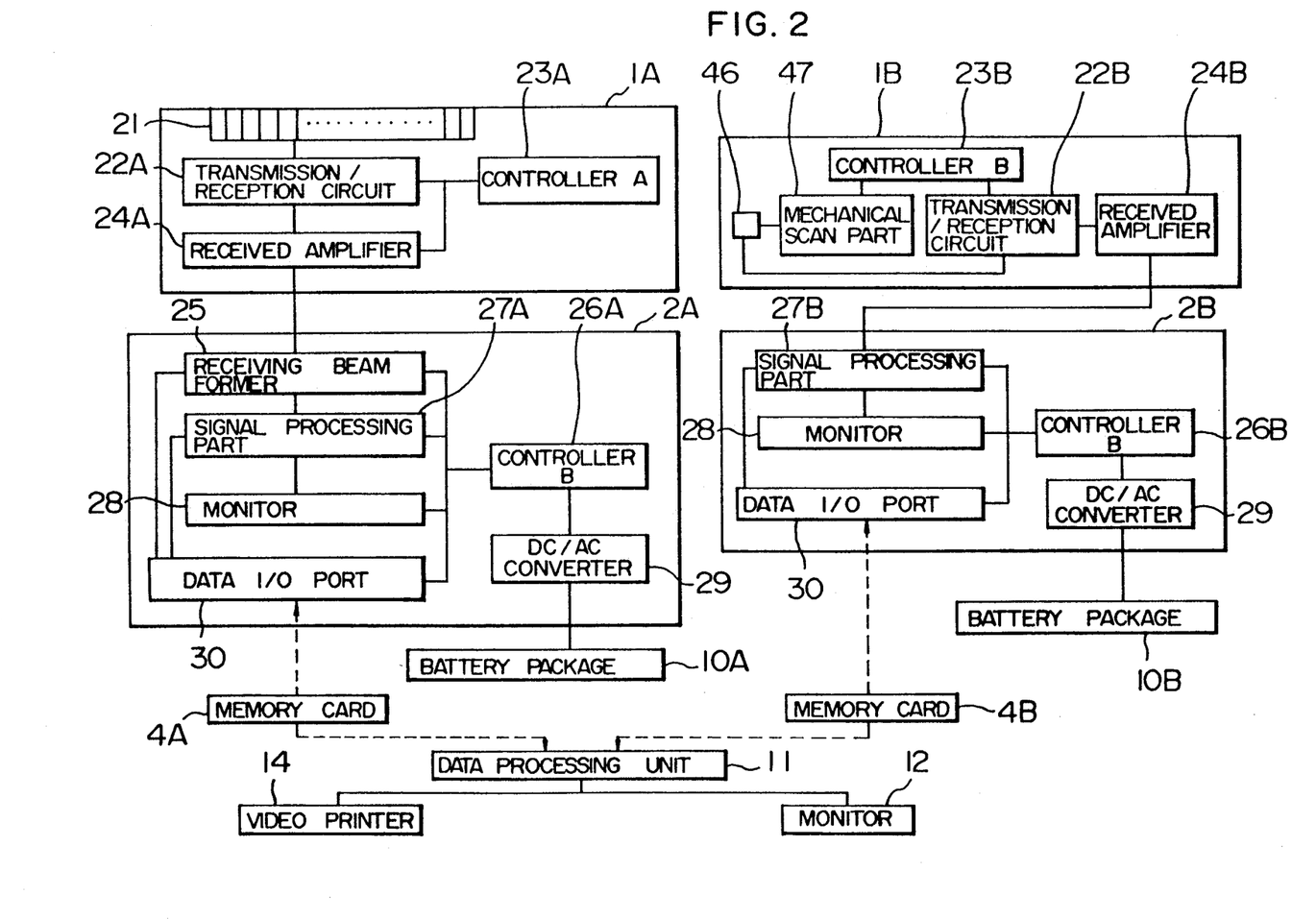
FIG. 2 is a block diagram showing the circuit configuration of one embodiment of the probe and main system according to the present invention.

Now referring to FIG. 2, this embodiment will be explained in more detail. FIG. 2 shows the detailed arrangement of the probe and main system, taking, as an example as in FIG. 1, the arrangement composed of a probe 1A dedicated to linear electronic scanning and the corresponding main system 2A, and another probe 1B dedicated to mechanical sector scanning and the corresponding main system 2B.

The linear electronic scanning probe 1A incorporates array transducers 21, a transmitted-and-received circuit 22A for transmitting/receiving an ultrasonic wave, a received amplifier 24A for amplifying the received ultrasonic wave and a controller A for controlling the transmitted-and-received circuit 22A and the received amplifier 24A. Thus, the signal lines as many as the transducers used for simultaneous transmission and reception are required to transmit the output from the received amplifier 24A to the main system 2A. The lines required in addition to these lines are only a power line for receiving the power supplied from the DC/AC converter 29 in the main system 2A to operate the probe 1A and a control line for transferring a control signal between the main system 2A and the probe IA. Therefore, the main system 2A and the probe 1A can be connected by flexible and light cables.

As an alternative arrangement, the main system 2A may include the transmitted-and-received circuit 22A and the received amplifier 24A, and in place of this, the probe 1A does not incorporate the electronic circuits such as the transmitted-and-received circuit 22A and the received amplifier 24A and includes only the array transducers 21. In this case, the probe 1A becomes small-sized, but the number of the signal lines for transmitting and receiving the ultrasonic wave increases so that the cable for connecting the probe IA and the main system becomes thick and heavy. But by converting several kinds of signals into optical signals and connecting the probe 1A and the main system 2A, this cable can be made thin. In this way, the signals may be transferred in the form of an optical or radio signal as well as the electrical signal.

The mechanical sector scanning probe 1B incorporates a transducer 46, a mechanical scan part 47 for mechanically scanning the transducer 46, a transmitted-and-received circuit 22B, a received amplifier 24B and a controller A 23B for controlling the mechanical scan part 47, transmitted-and-received circuit 22B and received amplifier 24B.

The main system 2A serves to process only the received signal data from the linear electronic scanning probe 1A. The main system 2A includes a receiving beam former 25 for forming the ultrasonic beam of the transmitted or received wave, a signal processing unit 27A for processing the received signal data, a monitor 28 for displaying the image relative to a person-to-be examined processed in the signal processing unit 27A, a data input/output (I/O) port 30 for transferring to the memory card 4A the information such as the image data or received signal data, patient information data, main system identification code, etc., a DC/AC converter 29 for converting the power supplied from the battery pack 10A into a necessary voltage, and a controller B 26A for controlling the receiving beam former 27A, signal processing unit 27A, monitor 28, data I/O port 30 and DC/AC converter 29.

The signal sent from the received amplifier 24A is signal-processed in four modes described below. In the first signal processing, the A/D-converted signal sent from the received amplifier 24A is recorded or stored, as it is, in the memory card 4A through the data I/O 30. In the second signal processing, the signal sent from the received amplifier 24A is signal-processed by the receiving beam former 25, and the progressing or final processing result is stored, in the form of digital data, in the memory card 4A through the data I/O port 30. In the third signal processing, the signal sent from the received amplifier 24A is signal-processed by the receiving beam former 25, and further signal-processed by the signal processing unit 27A to acquire image data to be displayed on the monitor 28 and also stored, in the form of digital data, in the memory card 4A through the data I/O port 30. In the fourth signal processing, a plurality of the first to the third processing are carried out.

Although the data storage in the memory card 4A is performed for the data for each desired image frozen or temporarily held, it may be carried out in such a manner that the desired images are successively stored in the memory card 4A.

The main system 2B serves to process and control only the received signal data sent from the mechanical sector scanning probe 1A. The main system 2B is different from the main system 2A in that it does not include the receiving beam former 25.

The signal sent from the received amplifier 24B is signal-processed in three modes described below. In the first signal processing, the A/D-converted signal sent from the received amplifier 24B is stored, as it is, in the memory card 4B through the data I/O port 30. In the second signal processing, the signal sent from the received amplifier 24B is signal-processed by the signal processing unit 27B to acquire image data to be displayed on the monitor 28 and also stored, in the form of digital data, in the memory card 4B through the data I/O port 30. In the third signal processing, both the first to the second processing are carried out.

As described above, the received signal taken in the signal processing units 27A or 27B is A/D converted as it is an RF signal or detected signal, and the digitized signal can be stored in the memory card 4A or 4B which is an external memory device.

The concrete configurations of the signal processing units 27A, 27B . . . and the controllers A, B, 26A, 26B . . . in the main systems are different with the ultrasonic scanning mode adopted. On the other hand, the monitors 28, data I/O ports and DC/AC converters 29 in the main systems are not greatly different with the ultrasonic scanning mode adopted, but substantially common to any ultrasonic scanning mode.

The signal processing units 27A and 27B . . . may be structured so as to be applied to several ultrasonic scanning modes such as linear electronic scanning, convex electronic scanning, sector electronic scanning, and mechanical sector scanning. But this increases their circuit scale so that in the present invention, they are structured so as to be applied to a specific ultrasonic scanning mode, respectively. Thus, the main systems 2A and 2B . . . can be simplified in circuit configuration, made small in size and light in weight, and also can be fabricated at low cost.

The signal processing units 27A and 27B . . . do not perform the processing of measuring length and area, but have only a simple function, e.g. a function of processing only a minimum ultrasonic image necessary to diagnose a person to be examined.

The received signal data stored in the memory cards 4A and 4B . . . essentially have the information more than that of the images displayed on the monitors 28 in the main systems 2A and 2B . . . . Thus, using the RF signal data or detected signal stored in the memory cards 4A and 4B . . . , the data processing unit 11 performs more sophisticated data processing to acquire several kinds of information.

Figure 3:
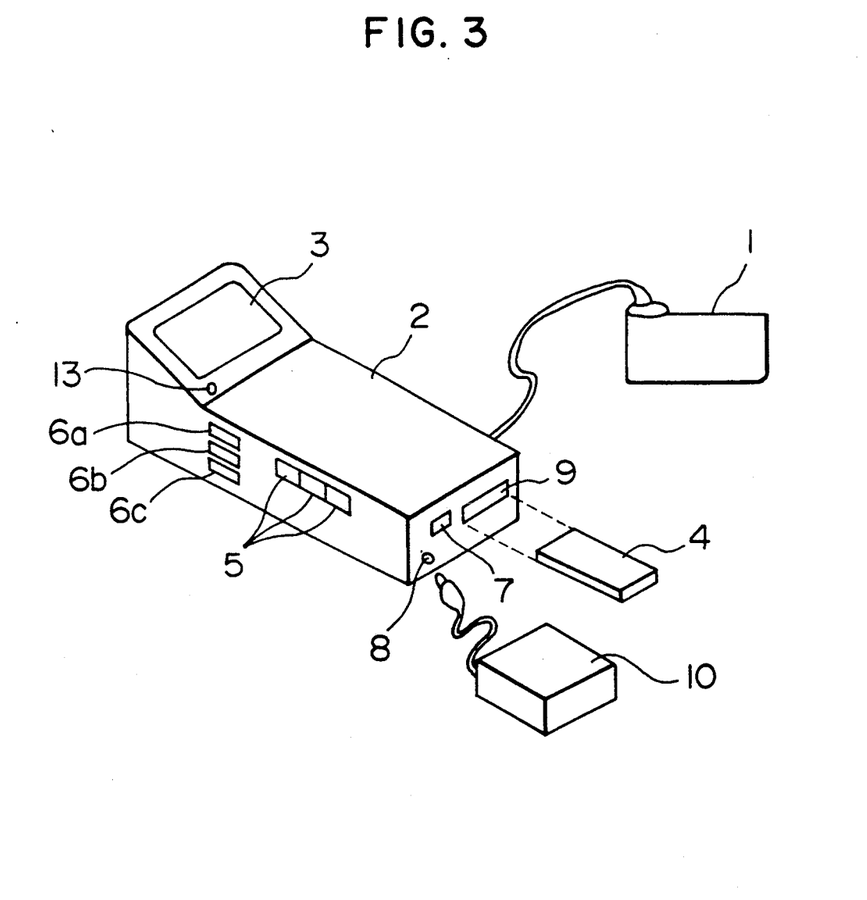
FIG. 3 is a perspective view showing one embodiment of the main system according to the present invention.

FIG. 3 pictorially shows an portable ultrasonic diagnostic system according to the present invention. The ultrasonic diagnostic system is mainly composed of a probe 1, a main system 2, a battery package 10 and a memory card 4. The main system 2 includes a display 3 such as a light-weight and low power type of flat panel including a liquid crystal panel. The main system 2 includes a gain control switch 5, a mode switch 6a, a freeze switch 6b, a data transmission switch 6c, a main switch 7, etc. The memory card 4 is mounted in a memory card connector 9 of the main system 2. The battery package 10 is connected with a power supply input connector 8 of the main system to supply power to the main system 2. In a state where the main switch 7 is "on", power is supplied so that the main system 2 is operable.

The mode switch 6a serves to designate the mode of signal processing such as the first to the fourth or third signal processing described in connection with FIG. 2. The freeze switch 6b serves to freeze or temporarily hold a desired image temporarily to display it as a still image. When the data transmission switch 6c is turned on, the image data or received signal data are transferred to the memory card 4. The gain control switch 5 serves to control the signal gain. An indicator 13, which is lit while the data are transferred, indicates that the data are now being transferred, thereby permitting the transfer/storage of the data to be recognized. When the freeze switch 6b and the data transmission switch 6c are simultaneously turned on, freezing of the image and transmission of the image data can be repeated successively. On the other hand, when the freeze switch 6b and the data transmission switch 6c are turned off, freezing of the image and transmission of the image data are stopped.

These switches are arranged so that they are easily operated with one hand. FIG. 3 shows an arrangement in which with the main system carried on a left hand, these switches can be operated with the thumb. These switches may be arranged on the side opposite to that in FIG. 3 so that they can be operated with the remaining fingers. An examiner operates the probe 1, kept in contact with a patient's body, with his right hand, and operates the main system 2 with his left hand. Of course, the right and left hands may be reversed.

Figure 4:
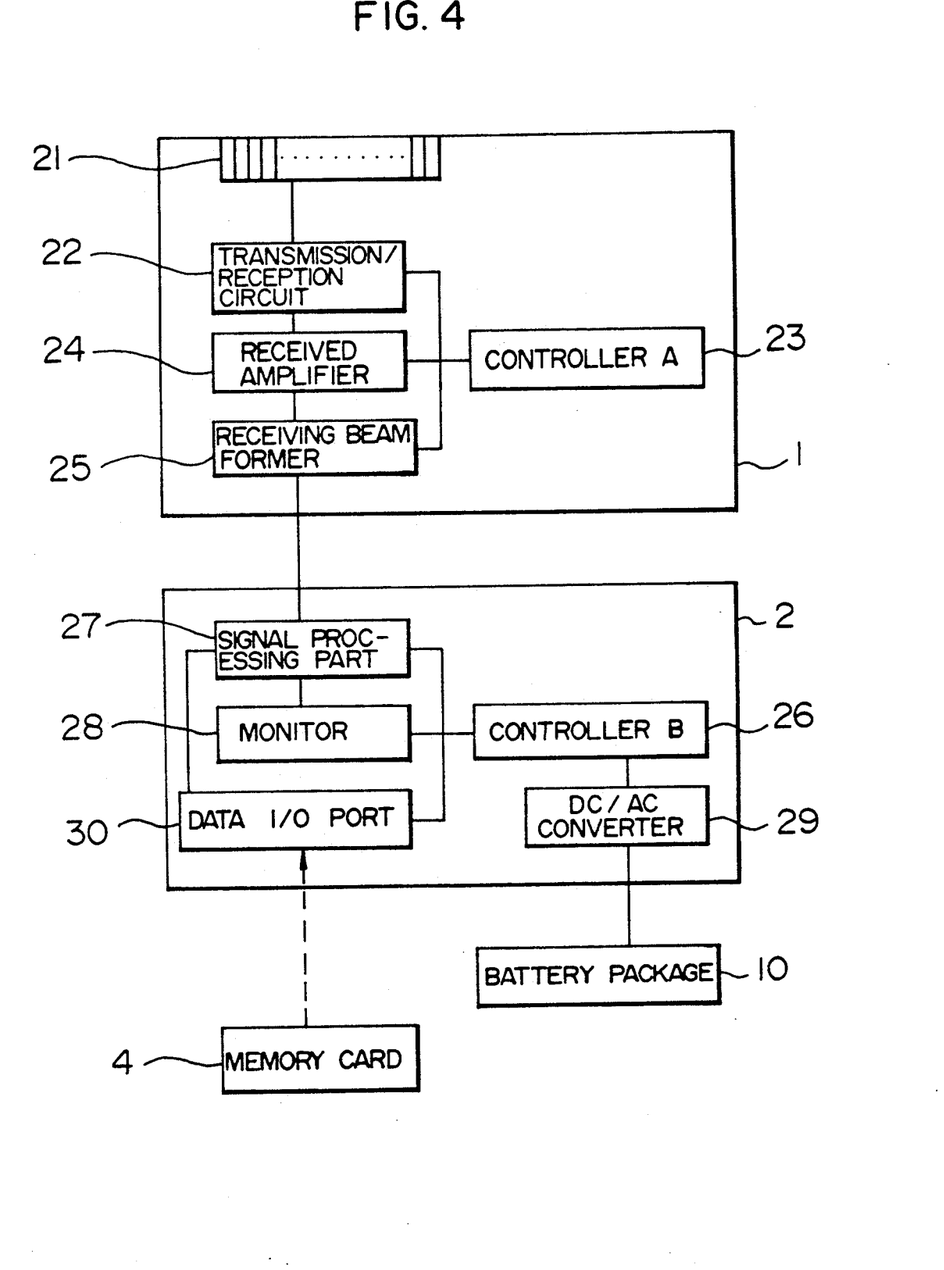
FIG. 4 is a block diagram showing another embodiment of the probe and main system according to the present invention.

FIG. 4 shows a configuration of a linear electronic scanning probe 1 and the corresponding main system 2 in which the RF signal or detected signal is directly supplied to a memory card 4. This configuration is realized by directly leading the output from a receiving beam former 25 to an image data I/O port. Where the memory card 4 is a digital memory card, it is needless to say that the RF signal or detected signal has been converted into a digital signal before it is stored in the memory card. Where the memory card 4 is an analog memory card, the RF signal or detected signal is stored, as it is without being converted into a digital signal, in the memory card.

The linear electronic scanning probe 1 incorporates array transducers 21, a transmitted-and-received circuit 22 for transmitting/receiving an ultrasonic wave, a received amplifier 24 for amplifying the received ultrasonic wave, a receiving beam former 25 for forming the ultrasonic beam of the transmitted and received wave and a controller A 23 for controlling the transmitted-and-received circuit 22, received amplifier 24 and receiving beam former 25. The receiving beam former 25 is incorporated in the probe 1. The receiving beam former 25 synchronizes phases of the received signals one another and then adds the received signals to output an output signal. Thus, only one signal line is required to transmit the output from the receiving beam former 25 to the main system 2. The lines required in addition to this line are only a power line for receiving the power supplied from the DC/AC converter 29 in the main system 2 to operate the probe 1 and a control line for transferring a control signal between the main system 2 and the probe 1. Therefore, the main system 2 and the probe 1 can be connected by flexible and light cables.

The main system 2 can control only the linear electronic scanning probe 1 and serves to process only the received signal data from the probe 1. The main system 2A includes a signal processing part 27 for processing the received signal data, a monitor 28 for displaying the image relative to a person-to-be examined, a data input/output (I/O) port 30 for transferring to the memory card 4 the information such as the image data, or the RF signal data or detected signal data necessary to create an image, patient information data, main system identification code, etc., a DC/AC converter 29 for converting the power supplied from the battery package 10 into a necessary voltage, and a controller B 26 for controlling the signal processing part 27, monitor 28, data I/O port 30 and DC/AC converter 29.

The signal sent from the receiving beam former 25 is signal-processed in three modes described below. In the first signal processing, the A/D-converted signal sent from the receiving beam former 25 is stored, as it is, in the memory card 4 through the data I/O port 30. In the second signal processing, the signal sent from the receiving beam former 25 is signal-processed by the signal processing unit 27 to acquire image data to be displayed on the monitor 28 and also stored, in the form of digital data, in the memory card 4A through the data I/O port 30. In the third signal processing, both the first to the second processing are carried out.

As described above, the received signal taken in the signal processing part 27 is A/D converted, as it is an RF signal or detected signal, and the digitized signal can be stored in the memory card 4 which is an external memory device.

The signal processing unit 27 may be structured so as to be applied to several ultrasonic scanning modes such as linear electronic scanning, convex electronic scanning, sector electronic scanning, and mechanical sector scanning. But this increases its circuit scale so that in the present invention, they are structured so as to be applied to a specific ultrasonic scanning mode. Thus, the main system 2 can be simplified in circuit configuration, made small in size and light in weight, and also can be fabricated at low cost. Where the scanning for the probe in the other scanning mode can be controlled using a partial circuit function of the main system for a certain scanning mode and the probes are removable from the main system, it is needless to say that the main system can be used commonly.

It should be noted that the signal processing part 27 does not perform the processing of measuring length and area, but have only a simple function, e.g. a function of processing only a minimum ultrasonic image necessary to diagnose a person to be examined.

Figure 5:
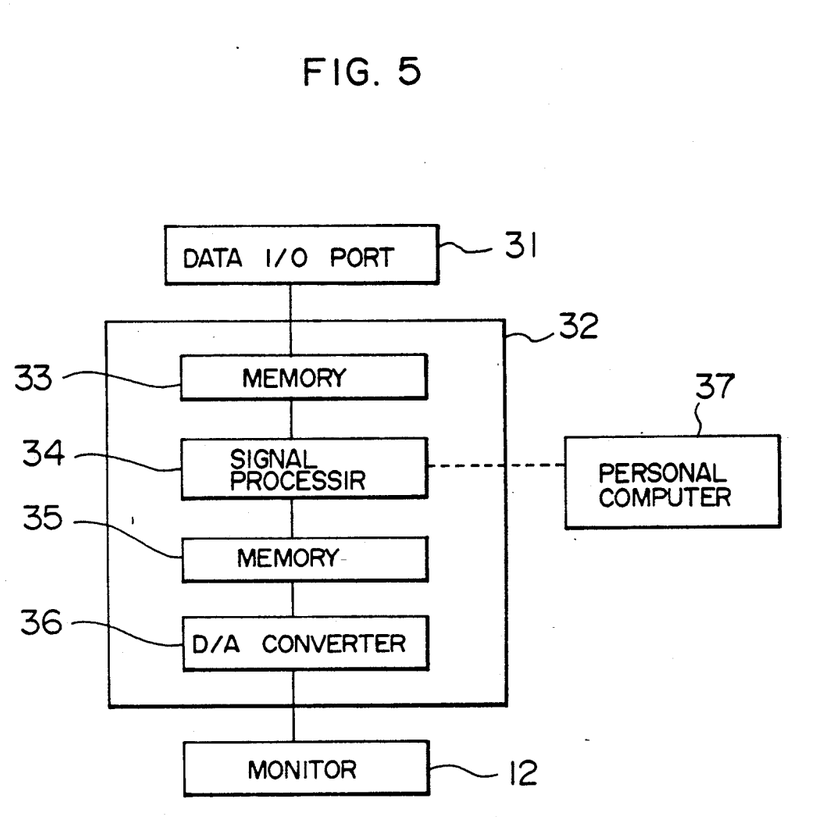
FIG. 5 is a block diagram showing one embodiment of the data processing unit according to the present invention.

FIG. 5 shows the basic configuration of the signal processing part in the data processing unit 11 which is provided separately from the main system. In operation, the information such as the image data or received signal data (RF signal data or detected signal data), patient information data, main system identification code, etc. is read from the memory card set in a data I/O port 31 in the data processing unit 11. The above information, particularly the main system identification code (ultrasonic scanning mode), is identified to perform the data processing in a data processing part 32. It is needless to say that the image data read from the memory card can be displayed on a monitor 12.

When a segment of the memory card with storage contents by the main system is designated, the ultrasonic scanning system is automatically identified in terms of the identification code of the main system stored in the designated segment to perform the data processing suited thereto automatically or under the condition set by an examiner.

Specifically, a signal processor 34 subjects the received signal data stored in memory 33 to the processing such as interpolation and the processing result is stored on memory 35. A D/A converter 36 converts the result into an analog signal to be sent to the monitor 12. The signal processor 34 also performs conversion for the scanning for the display of the monitor. The scan conversion, interpolation, processing for measuring an area and length and the data processing for the received signal data in the signal processor 34 can be also carried out using a personal computer 37.

The data processing unit 11 can be realized by a combination of a scan converter equipped with image memory, monitor, a read device for the memory card with a computer. The ultrasonic diagnostic system equipped with a read device for the memory card can be used as the data processing unit 11.

The received signal data stored in the memory card is subjected to not only the data processing by the main system but also more sophisticated data processing by the data processing part 32 in the data processing unit 11. The result is displayed as an image on the monitor or supplied to several kinds of memory devices. For example, a high quality image can be displayed on a high resolution image output device. Thus, by means of the data processing unit 11, the examiner can fulfill the processing (e.g. advanced interpolation processing, echo enhancement, γ-correction, optimization of a gain curve, correlation process, etc.) equivalent or more to a high performance ultrasonic diagnostic system thereby to obtain the high resolution image relative to a person to be examined, including advanced diagnosis information.

Thus, by means of the data processing unit 11, the examiner can convert the image noticed at bedside or in diagnosis such as house call into a more accurate diagnosis image through measurement processing for several kinds of items such as a length, volume, area, attenuation, sound velocity and blood velocity, advanced interpolation processing, echo enhancement, γ-correction, optimization of a gain curve, etc. The data processing result obtained by the data processing unit 11 can be stored in the memory card.

Figure 6:
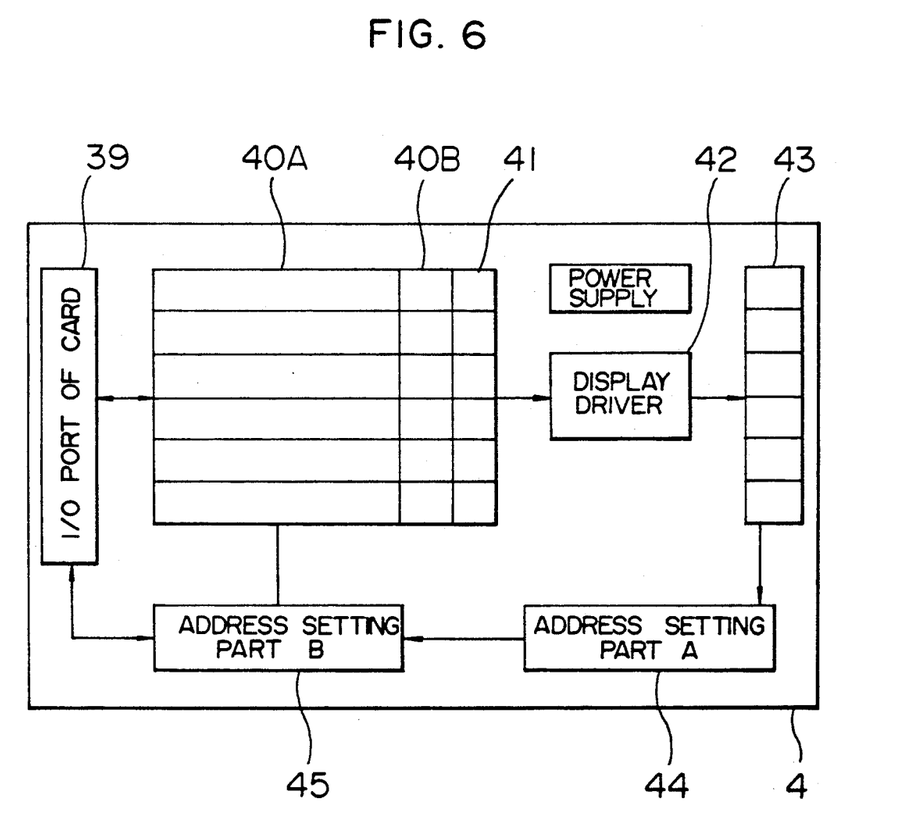
FIG. 6 is a block diagram showing one embodiment of the memory card according to the present invention.

Now referring to FIG. 6, the memory card used in the present invention will be explained. The memory card 4 transfers the received signal data and several kinds of information to/from the main system and data processing unit 11 through a card I/O port 39. The memory card 4 includes a data record part where at least one of one image data, and a received signal data (an RF signal data or detected signal data necessary to create one image) is recorded, and an information record part where a main system identification code (for identifying the ultrasonic scanning mode), patient information data (e.g. ID's corresponding to a diagnosis date, examiner's name and patient's name, carte number, and disease history). The memory card 4 has memory divided into plural segments (storage areas) each having a prescribed memory size composed of the data record part 40A, the information record part 40B and a flag record part 41 for recording the presence or absence of data storage. The memory card 4 also includes a segment display part which serves to display whether or not the data have been stored in each segment and can designate the segment which data should be stored in or erased from.

Now for brevity of explanation, it is assumed that the memory of the memory card is divided into six segments and the memory can store the most possible six image data or the received signal data to create six images. The segment display part 43 is composed of switches and light emitting devices such as light emitting diodes.

When a data is inputted, it is stored in the first segment of the memory. Then, a flag representing that the data has been stored in the memory is recorded in the corresponding area of the flag recorded part 41. This flag drives a display driver 42 so that the light emitting diode in the segment display part 43 corresponding to the first segment of the memory emits light. The segment display part 43 is connected with the data I/O port of the main system 2 or the data I/O port 31 of the data processing unit 11 so as to operate. Using the switch in the segment display part 43, an examiner can designate the segment in which data is to be stored. When a certain segment is designated, an address setting part A 44 sets the start address of the designated segment and an address setting part B 45 stores the data in the designated segment. Provision of erasure switches permits the segment from which data is to be erased to be designated. If the switch for operating the segment display part 43 separately attached to the memory card is turned on, the storage state of the segments can be known by the memory card itself. It is needless to say that the memory card is provided with a power supply necessary to operate its various parts.

The segment display part 43 may be a combination of a liquid crystal panel and a touch panel. Further, all or part of the operation of designating a segment as described above may be carried out by the main system 2 or data processing unit 11. In this case, the memory card itself is not required to include the segment display part 43. Furthermore, the storage format adopted for the memory is composed of the data record part where the image data or the received signal data is recorded, the information record part where the main system identification code, patient information data, etc. are recorded and the flag record part where the presence or absence of storage in the segments, but other storage formats may be adopted. Further, it is possible to reduce the amount of recorded information by passing the data or information through a suitable information compressing means (not shown) before they are recorded.

Figure 7A:
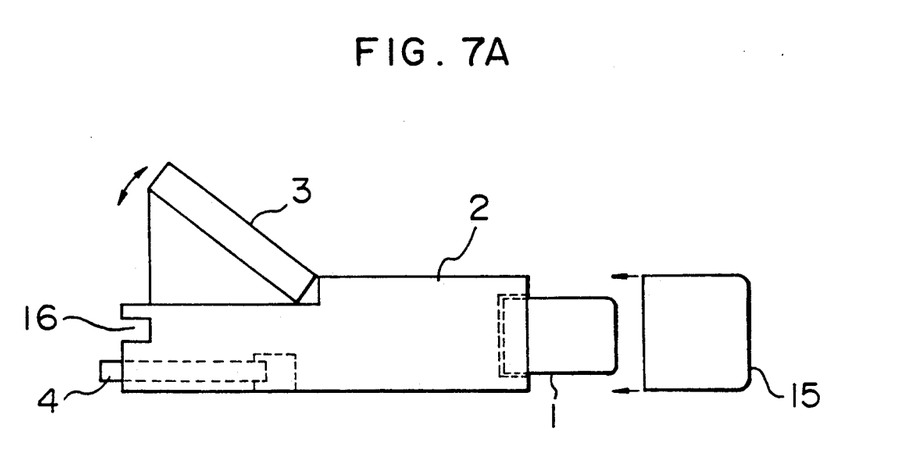
FIG. 7A is a side view showing another embodiment of the main system according to the present invention.
Figure 7B:
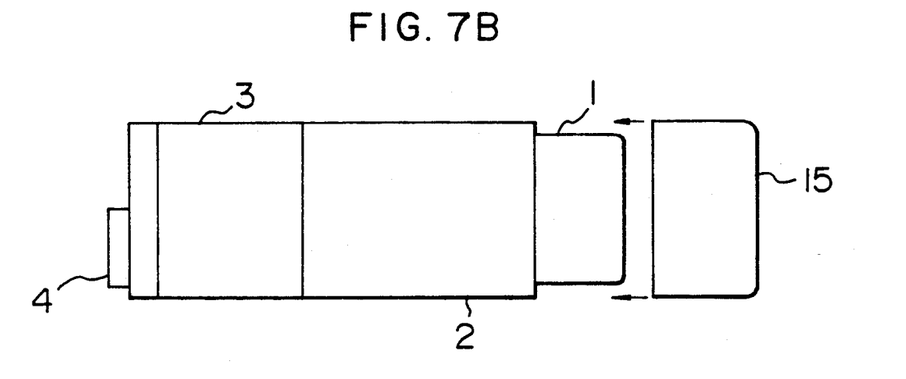
FIG. 7B is a plan view showing another embodiment of the main system according to the present invention.

Another example of the main system 2 which is different from that of FIG. 3 will be explained. FIG. 7A is a side view of the main system 2 and FIG. 7B is a plan view thereof. A display 3 is made so as to be movable in the direction indicated in FIG. 7A. If the display 3 is stood when the main system is used and restored to an original position when it is not used, the external shape of the main system 2 forms a uniform surface. A flat panel, which was described as being used as the display in the explanation of FIG. 3, may be attached to the main system so that it is rotatable freely. A housing space in which the probe 1 is to be housed is provided at a portion of the main system. A protector 15 is attached to the main system 2 to protect the probe 1 and improve its movableness. The memory card 4 is carried as it is housed in the main system 2.

Figure 7C:
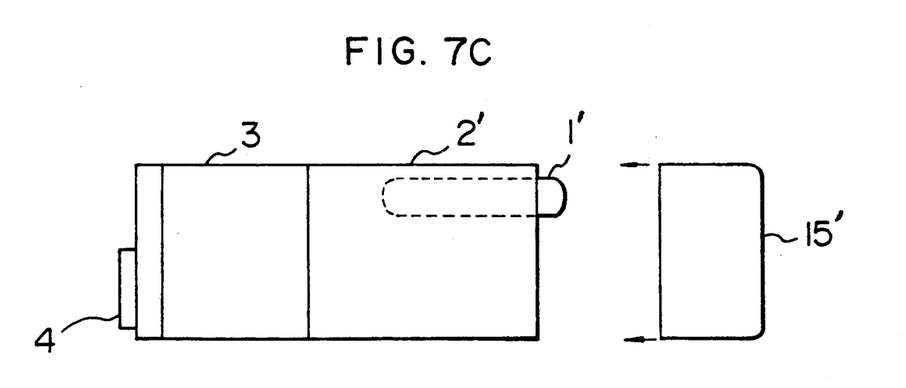
FIG. 7C is a plan view of the main system showing an example of housing the probe according to the present invention.

A card reader 16 serves to read the ID card or electronic chart card in which a patient number, an ID number, a chart number, disease history, etc. are recorded. Only predetermined necessary data of the data recorded in the ID card or electronic chart card are recorded in the beginning of the segments with no storage or the area of the information data part 40B of a designated segment. FIG. 7C is a plan view of a main system 2' in which a sector scanning ultrasonic probe (mechanical or annular array probe) 1' is stored. In this example also, a housing space in which the probe 1 is to be housed is provided at a portion of the main system 2', and a protector 15' is attached to the main system 2' to protect the probe 1' and improve its movableness.

Incidentally, in FIGS. 7A, 7B and 7C which mainly illustrate the external shape of the main system, several switches as shown in FIG. 3 are not shown for brevity of illustration.

Figure 8A:
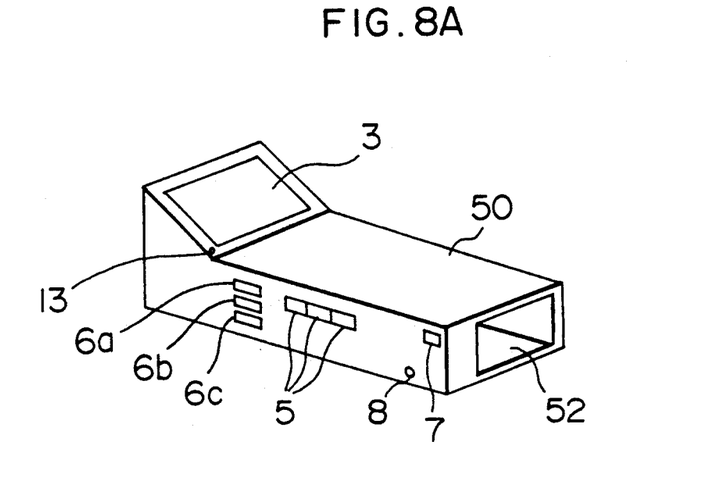
FIG. 8A is a perspective view showing the common body which can be used irrespectively of the ultrasonic scanning mode according to the present invention.
Figure 8B:
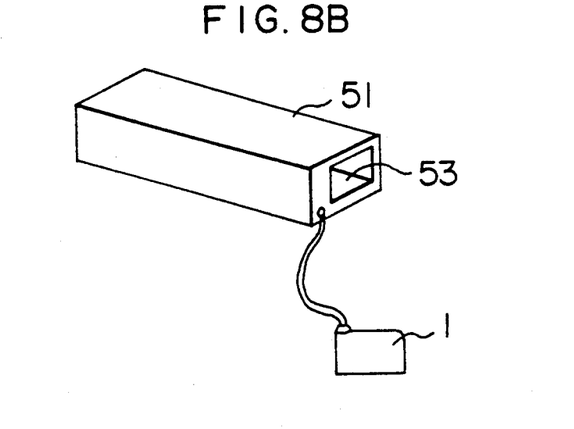
FIG. 8B is a perspective view showing the main system cartridge which is different with the scanning mode according to the present invention.

An explanation will be given of an embodiment of the main system which is structured using a common body commonly usable irrespectively of the ultrasonic scanning mode. As shown in FIG. 8A, the appearance of a common body 50 is similar to the main system 2 shown in FIG. 3. The common body 50 includes switches 5, 6a, 6b, 6c and 7 operated by an examiner, a display 3, a DC/AC converter, a data I/O part, a power supply input connector 8, etc., and can be commonly used for a main system cartridge 51 in any ultrasonic scanning mode described below. The main system cartridge 51 is connected with a probe 1 which is different with ultrasonic scanning modes, and includes a signal processing part, a receiving beam former, a controller B, etc. The main system cartridge 51 is previously fabricated as a separate body so that it can be inserted into an insertion port 52 of the main system 2 to be connected with the main system by a connector. The main system cartridge 51 is fabricated for each of different ultrasonic scanning modes. The main system cartridge 51 is provided with a probe house 53 in which the probe is to be housed. It is needless to say that the probe 1, after it is housed, is covered with a protector as in FIG. 7. The probe 1 and the main system cartridge 51 are connected by a connector and a cable; otherwise they may be directly connected by a cable without using a connector so that they are integrated. The main system cartridge 51 selected in accordance with the ultrasonic scanning mode is inserted into the insertion port 52 to be connected with the common body 50. Thus, the main system corresponding to the ultrasonic scanning mode can be fabricated. In this way, the main system can be fabricated by combining the main system cartridge with the common body. For this reason, even where diagnosis is made in plural different ultrasonic scanning modes, an examiner has only to prepare necessary and minimum number of units and easily change the scanning mode into a different ultrasonic scanning mode at a diagnosis site. Thus, the movableness of the main system can be further improved.

In the above embodiment, the conventional ultrasonic diagnostic system itself may be substituted for the data processing unit 11 and the monitor 12. In this case, the main system 2 may be mounted as a part on the diagnostic system, and as necessity requires, it may be removed and carried.

In the description hitherto made, the external memory device was described as a memory card. But, more specifically, the external memory device may be any of an IC card, an optical card capable of reading or writing information using laser light, a magnetic card, a floppy disk and a magnetic-optical disk. The IC card requires the capacity of 512 k words or so for each image where the RF signal after beam forming/addition is to be recorded. Assuming that one word is composed of 8 bits, the IC card of 4M byte theoretically permits the data of 7 images to be recorded but actually, it can only record the data of images fewer than 7 owing to record of patient information. Where image data are to be recorded, assuming that each image is displayed by $256 \times 512 \times 8$ bits, the data of about 1M bits are required for each image. Thus, each card can record the data for 20 or more images. Before beam forming/addition, the capacity required is the aperture number of times after beam forming/addition, or symmetrical beams require its half capacity. Therefore, although it is different with the scanning mode, where the required data cannot be recorded in one card in the scanning mode requiring a large amount of storage capacity, a function of recording the data divisionally in two or more cards is provided to the main system. Otherwise, two data I/O ports for inputting/outputting data in a manner of setting an external memory device in the main system may be provided. In this case, two IC cards are set in the main system to record the data. If the required data cannot be recorded in one IC card, the data I/O port is changed from one to the other to record the data in the other IC card. Usually, the external memory device is desired to have the capacity of 1M bytes or more.

In one format, the portable diagnostic system has such a shape as an examiner can carry it by one hand and operate its several switches by one hand. For example, in the shape as shown in FIG. 3, the system is desired to have weight of 1 kg, a length of 25 cm or less, a width of 12 cm or less and a height of 5 cm and a cable having a length of about 1 m. In another format, the system may be provided with a display panel having a size of about 9 inch and a keyboard panel like a lap-top personal computer so that it can be operated on an examiner's knees, a bed or desk.

As described above, in accordance with the present invention, a data processing unit for performing sophisticated signal processing and a data output/display device are provided separately from a main system, and the main system and a probe connected therewith are dedicated to each ultrasonic scanning mode so that the main system can be made compact and a handy ultrasonic diagnostic system can be realized, thereby permitting an examiner to use the diagnostic system instead of a stethoscope.

Further, since the main system can be fabricated by combining a main body which can be used irrespectively of the ultrasonic scanning mode and a main system cartridge which is different with the ultrasonic scanning mode, even where diagnosis is made in plural different ultrasonic scanning modes, an examiner has only to prepare necessary and minimum number of units and easily change the scanning mode into a different ultrasonic scanning mode at a diagnosis site. Thus, the movableness of the main system can be further improved.

In the system configuration and memory card according to the present invention, the main system can be made compact, the received data or image data can be recorded on the memory card and the high quality image acquired by the data processing unit for sophisticated data processing provided separately from the main system can be outputted to a high resolution image output device. Thus, high resolution and advanced diagnosis information can be obtained.

We claim:

1. An ultrasonic diagnostic system for transmitting and receiving an ultrasonic wave to display a sectional image of a body to be examined, comprising:
   a main system composed of a signal processing part utilized in a specific ultrasonic beam scanning mode for processing received signal data to acquire an image, a display utilized in a specific ultrasonic beam scanning mode for displaying the image acquired, a data I/O port for sending at least a main system code representing a specific ultrasonic beam scanning mode and the received signal data to an external memory device for storing time;
   a probe connected with said main system and having a transducer array for transmitting and receiving the ultrasonic wave;
   a data processing unit provided separately from said main system, said processing unit for reading at least said main system code and said received signal data from said external memory device to perform data processing for obtaining diagnosis information; and
   a monitor for displaying said diagnosis information.

2. An ultrasonic diagnostic system according to claim 1, wherein said probe and said main system are fabricated as individual members and are connected by a cable or connector.

3. An ultrasonic diagnostic system according to claim 1, wherein power is supplied from a DC power supply provided separately from said main system.

4. An ultrasonic diagnostic system according to claim 1, wherein at least one of said received signal data and image data processed by said signal processing part are recorded on said external memory device.

5. An ultrasonic diagnostic system according to claim 1, wherein plural time-successive image data processed by said signal processing part are recorded on said external memory device.

6. An ultrasonic diagnostic system according to claim 1, wherein said external memory device includes plural segments each having a predetermined memory size for recording said received signal data or the image data processed by said signal processing part and said main system code, and a display part for displaying whether each of said segments has an record or not.

7. An ultrasonic diagnostic system according to claim 1, wherein said external memory device has means for designating the segment which said received signal data or the image data processed by said signal processing part and the main system code are recorded on or erased from.

8. An ultrasonic diagnostic system according to claim 1, wherein said external memory device is any of an IC card, an optical card, a magnetic card, a floppy disk and a magnetic-optical disk.

9. An ultrasonic diagnostic system for transmitting and receiving an ultrasonic wave to display a sectional image of a body to be examined, comprising:
   a main system composed of a signal processing part utilized in a specific ultrasonic beam scanning mode for processing received signal data to acquire an image, a display utilized in a specific ultrasonic beam scanning mode for displaying the image acquired, a data I/O port for recording at least a main system code representing an ultrasonic beam mode and at least one of the received signal data and the image data processed by said signal processing part on an external memory device for storage thereof;
   a probe connected with said main system and having a transducer array for transmitting and receiving an ultrasonic wave;
   a data processing unit provided separately from said main system, said processing unit for reading at least said main system code and at least one of said received signal data and the image data processed by said signal processing part from said external memory device and deciding said ultrasonic beam scanning mode on the basis of said main system code to perform data processing for obtaining diagnosis information; and
   a monitor for displaying said diagnosis information.

10. An ultrasonic diagnostic system according to claim 9, wherein plural time-successive image data processed by said signal processing part are recorded on said external memory device.

11. An ultrasonic diagnostic system according to claim 9, wherein patient information data are recorded on said external memory device.

12. An ultrasonic diagnostic system according to claim 9, wherein said external memory device includes plural segments each having a predetermined memory size for recording said received signal data or the image data processed by said signal processing part and said main system code, and a display part for displaying whether each of said segments has a record or not.

13. An ultrasonic diagnostic system according to claim 9, wherein said external memory device has means for designating the segment which the said received signal data or image data processed by said signal processing part and said main system code are recorded on or erased from.

14. An ultrasonic diagnostic system according to claim 9, wherein said external memory device is any of an IC card, an optical card, a magnetic card, a floppy disk, a magnetic-optical disk.

15. An ultrasonic diagnostic system for transmitting and receiving an ultrasonic wave to display a sectional image of a body to be examined, comprising:
   a main system composed of a signal processing part utilized in a specific ultrasonic beam scanning mode for processing received signal data to acquire an image, a display for displaying the image acquired, a data I/O port for recording at least a main system code representing an ultrasonic beam scanning mode and the received signal data on an external memory device for storing them;
   a probe connected with said main system and having a transducer array for transmitting and receiving the ultrasonic wave;
   a data processing unit provided separately from said main system, said processing unit for reading at least said main system code and said received signal data from said external memory device and deciding said ultrasonic beam scanning mode on the basis of said main system code to perform data processing for obtaining diagnosis information; and a monitor for displaying said diagnosis information;

wherein said display and said data I/O port which can be commonly used irrespectively in the ultrasonic scanning mode and attached to a common body, and a main system cartridge which is separate from said common body and composed of circuit units including said signal processing part dedicated to a specific ultrasonic scanning mode is inserted into said common body so that it can be connected with said common body, whereby said main system can be applied to a specific ultrasonic beam scanning mode.

16. An ultrasonic diagnostic system according to claim 15, wherein said external memory device includes plural segments each having a predetermined memory size for recording said receive signal data or the image data processed by said signal processing part and said main system code, and a display part for displaying whether each of said segments has a record or not.

17. An ultrasonic diagnostic system according to claim 15, wherein said external memory device has means for designating the segment which the said received signal data or image data processed by said signal processing part and said main system code are recorded on or erased from.

18. An ultrasonic diagnostic system for transmitting and receiving an ultrasonic wave to display a sectional image of a body to be examined, comprising:

a main system composed of a signal processing part utilized in a specific ultrasonic beam scanning mode for processing received signal data to acquire an image, a display for displaying the image acquired, a data I/O port for recording at least a main system code representing an ultrasonic beam scanning mode and the received signal data and/or the image data processed by said signal processing part on an external memory device for storage thereof;

a probe connected with said main system and having a transducer array for transmitting and receiving the ultrasonic wave;

a data processing unit provided separately from said main system, said processing unit for reading at lest said main system code and said received signal data and/or the image data processed by said signal processing part from said external memory device and deciding said ultrasonic beam scanning mode on the basis of said main system code to perform a data processing for obtaining a diagnosis information; and a monitor for displaying said diagnosis information;

wherein said display and said data I/O port which can be commonly used irrespectively in the ultrasonic beam scanning mode are attached to a common body, and a main system cartridge which is separated from said common body and composed of circuit units including said signal processing part dedicated to a specific ultrasonic beam scanning mode is inserted into said common body so that it can be connected with said common body, whereby said main system can be applied to a specific ultrasonic beam scanning mode.

19. An ultrasonic diagnostic system according to claim 18, wherein said external memory device includes plural segments each having a predetermined memory size for recording said received signal data or the image data processed by said signal processing part and said main system code, and a display part for displaying whether each of said segments has a record or not.

20. An ultrasonic diagnostic system according to claim 18, wherein said external memory device has means for designating the segment which the said received signal data or image data processed by said signal processing part and said main system code are recorded on or erased from.

* * * * *